United States Patent
Nelson

(10) Patent No.: US 7,319,233 B2
(45) Date of Patent: Jan. 15, 2008

(54) SYSTEM, DEVICE, AND METHOD FOR DETECTING AND CHARACTERIZING EXPLOSIVE DEVICES AND WEAPONS AT SAFE STANDOFF DISTANCES

(75) Inventor: Mitchell C. Nelson, Morristown, NJ (US)

(73) Assignee: Material Intelligence, LLC, New York, NY (US)

(*) Notice: Subject to any disclaimer, the term of this patent is extended or adjusted under 35 U.S.C. 154(b) by 0 days.

(21) Appl. No.: 11/234,663

(22) Filed: Sep. 23, 2005

(65) Prior Publication Data

US 2007/0262275 A1 Nov. 15, 2007

Related U.S. Application Data

(60) Provisional application No. 60/683,494, filed on May 20, 2005, provisional application No. 60/612,555, filed on Sep. 23, 2004.

(51) Int. Cl.
*G01N 21/86* (2006.01)
*G01N 21/88* (2006.01)
*G01V 8/00* (2006.01)
*G01S 13/00* (2006.01)

(52) U.S. Cl. ...................... 250/559.4; 342/22
(58) Field of Classification Search ............. 250/559.4; 342/22, 27, 90; 356/335, 336
See application file for complete search history.

(56) References Cited

U.S. PATENT DOCUMENTS 5,367,552 A * 11/1994 Peschmann .................. 378/57
5,692,029 A * 11/1997 Husseiny et al. ............. 378/88

* cited by examiner

*Primary Examiner*—Thanh X. Luu
*Assistant Examiner*—Suezu Ellis
(74) *Attorney, Agent, or Firm*—Law Offices of Mitchell P. Novick

(57) ABSTRACT

Apparatus that invention detects and characterizes hard or metallic materials or objects, worn or carried by persons or concealed on their persons or in bags or luggage, using directed or propagated energy such as ultrasound or microwave, that is reflected or scattered by the materials and objects of interest and that has a wavelength or wavelengths such that the width and/or shape of the reflected beam can be measured at the desired detection distance or range of distances and has a measurable dependence on the size and/or shape of the object, utilizing diffraction methods. Also disclosed are a system and a method utilizing this apparatus.

2 Claims, 8 Drawing Sheets

SYSTEM, DEVICE, AND METHOD FOR DETECTING AND CHARACTERIZING EXPLOSIVE DEVICES AND WEAPONS AT SAFE STANDOFF DISTANCES

CROSS REFERENCES TO RELATED APPLICATIONS

This application claims the benefit of U.S. Provisional Patent Application Ser. Nos. 60/612,555, filed 23 Sep. 2004; and 60/683,494, filed 20 May 2005, the contents of which are incorporated into this application as if set forth in detail herein.

FIELD OF THE INVENTION

Embodiments of the present invention related to an apparatus, system, and method of detection and location from safe distances (for example 30 meters), of persons carrying explosive devices or weapons. Certain embodiments are designed to be used in public places.

BACKGROUND OF THE INVENTION

Terrorist explosive devices have produced the largest portion of terrorist casualties among civilian and military personnel compared to all other terrorist tactics. Commonly, the weapons used in such terrorist attacks are exploding vests and remotely detonated anti-personnel devices.

Numerous types of apparatus and methods have been utilized to detect and characterize such explosive devices, for example millimeter wave imaging, passive terahertz imaging, infrared imaging, trace chemical detection.

One such approach is imaging. But imaging techniques, by their nature, incur significant costs in exposure time and distance to produce information that is minimally relevant and not easily interpreted. Passive imaging systems are further challenged by low flux and high background.

Another approach is "sniff and wipe" technology. This technique relies on traces of specific explosives in air or on surfaces. However, bombers are using those same commercial sniffers and gateways to help them test their devices to evade trace detection.

Specific prior art technology includes:

1. Passive Imaging of Millimeter Wave Radiation.

Humans are said to be natural emitters of millimeter wave radiation. Camera-like systems for imaging millimeter wave radiations are reportedly under development or being offered by Millitech Corp. (Millivision), of South Deerfield, Mass. Detection of weapons and explosives and other concealed objects is said to be enabled by the differences in the amount of millimeter wave emission by those objects and humans and clothing. The drawbacks of this approach include that the images need to be interpreted by human operators or software. Also, exposure times are reported to be long.

2. Ultrasound for Remote Imaging of Concealed Weapons.

ATAG-Titan has developed a breadboard model of a system that is said to be able to detect metal and other hard objects under clothing at a distance of 8 m, and that can image objects at a distance of 5 m. However, operators need to be trained to interpret the images which are vague in appearance. Also, the 5 m distance is inadequate for safe explosives detection.

3. Chemical Trace Detection.

Several devices are marketed that detect trace chemicals from explosives or drugs. Most such devices are portal type or require mechanical contact with the subject and so are not directly related to this application. Variants are being developed that stimulate radiation from trace chemicals and so could be used at some distance. It seems likely that when such devices are deployed, the bomb makers will learn to remove trace chemicals from the exteriors of their devices.

4. IR Imaging.

IR imaging using IR pass filters in ambient light is also known art. Drawbacks of this approach include exposure times are long and/or the method can only to "see" through trivial thickness of clothing and/or at close range.

The prior art devices have significant shortcomings including long exposure times, low or non sensitivity to non-metallic materials, limited distances of operation. Trace chemical detection devices have further shortcomings in that explosive devices can be prepared in such a ways as to avoid trace detection.

BRIEF SUMMARY OF THE INVENTION

The purpose of the present invention is to provide a system, device, and method for detecting and characterizing explosive devices and weapons at distances sufficient to provide safety to those entrusted with the detection.

This invention utilizes some generalized characteristics of such explosive devices. While bomb makers of exploding vests and remotely detonated anti-personnel devices have shown considerable ingenuity in devising ways to deliver and detonate these devices, practical considerations dictate that these devices (1) are generally approximately 20 cm to 50 cm in size, (2) are overlaid by hard projectiles or casing materials, and (3) when concealed, are concealed in soft or loose materials.

This invention utilizes basic physical principles of scattering and reflection to detect and characterize targets with respect to criteria that are sufficient and relevant, with high sensitivity at large distances. This invention focuses on the criteria that are most directly related to the ability of a device to cause harm, and in so doing is able to optimize for sensitivity, real time response, and standoff distance.

Specifically, this invention detects and characterizes hard or metallic materials or objects, worn or carried by persons or concealed on their persons or in bags or luggage, using directed or propagated energy such as ultrasound or microwave, that is reflected or scattered by the materials and objects of interest and that has a wavelength or wavelengths such that the width and/or shape of the reflected beam can be measured at the desired detection distance or range of distances and has a measurable dependence on the size and/or shape of the object, utilizing diffraction methods.

This invention can display and locate multiple targets with resolution 1 mr×1 cm, displays the approximate size and shape of each target color coded for its hardness, and provides an indication of whether is concealed or carried openly. This invention preferably has a range of at least 1.5 m to 50 m for hand-held and tripod-mounted hardware.

DETAILED DESCRIPTION OF THE INVENTION

Figure 1:
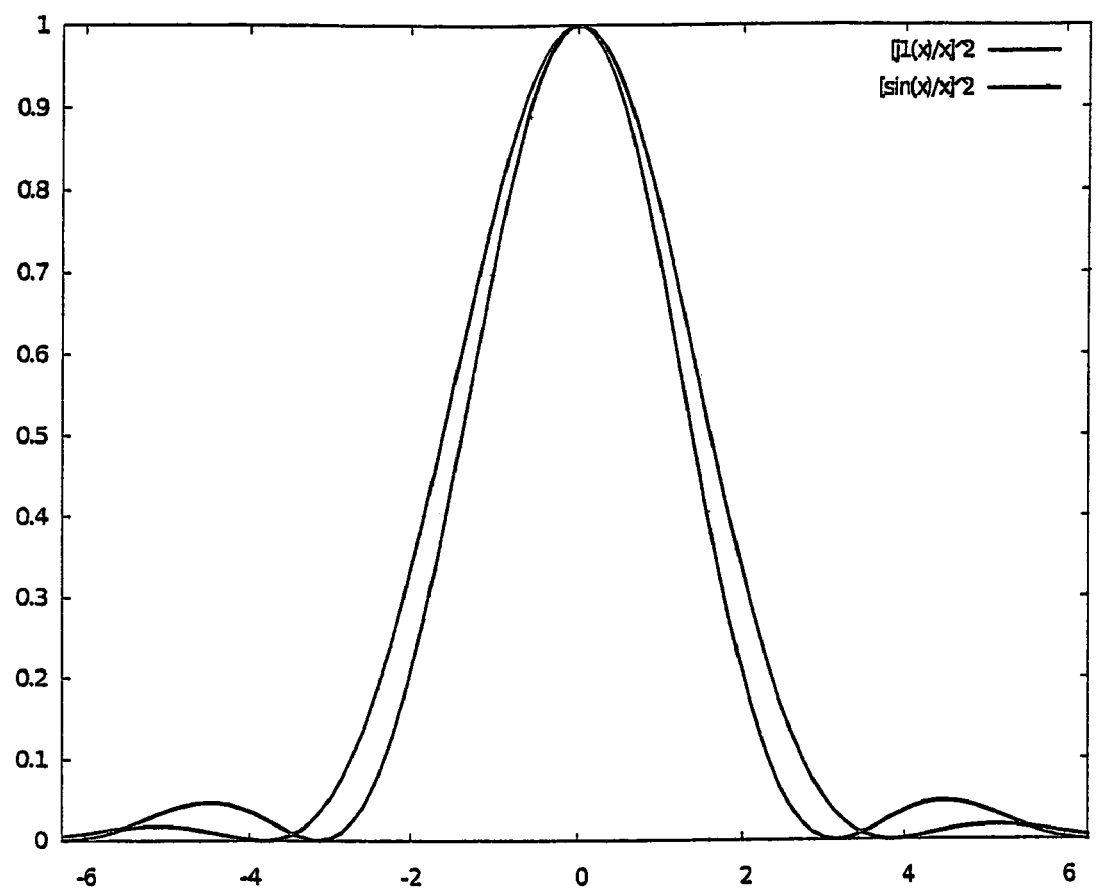
FIG. 1 is a graph a intensity verses angle for Fraunhofer diffraction by circular and rectangular surfaces and apertures.
Figure 2:
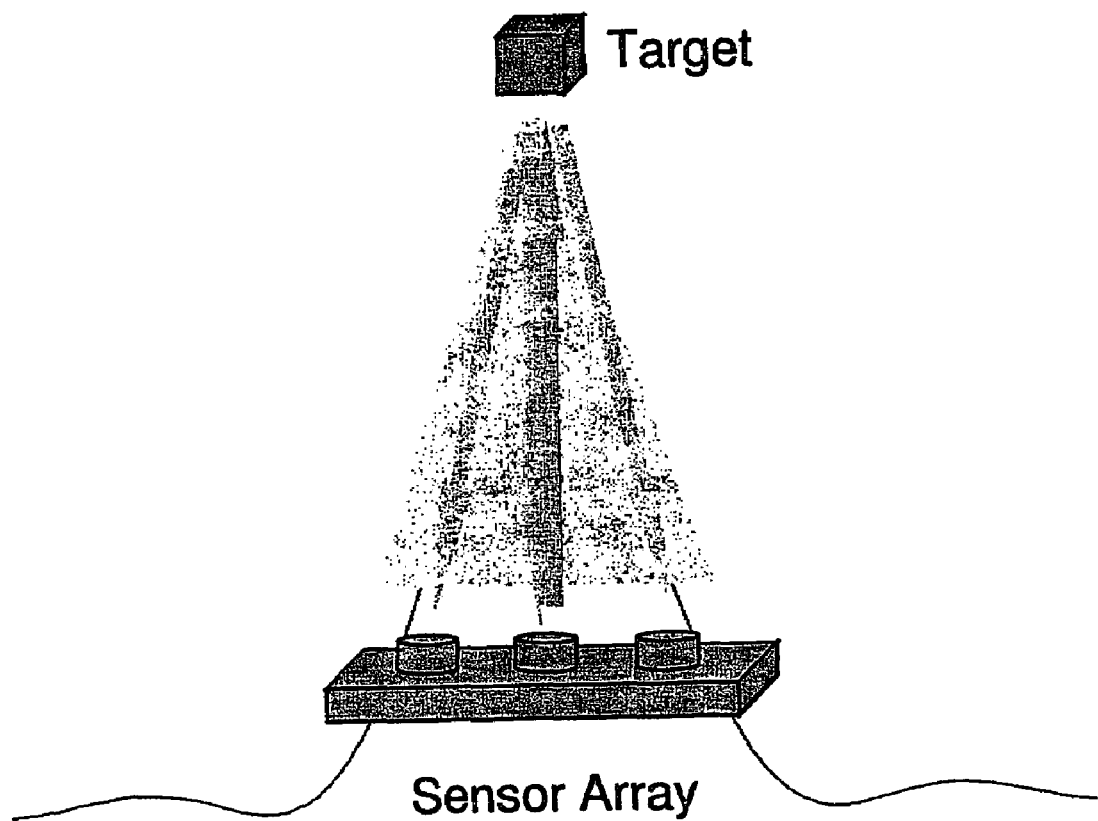
FIG. 2 is a schematic diagram of a 3 sensor array and a object to be detected (target).

The present invention detects and characterizes hard or metallic materials or objects, worn or carried by persons or concealed on their persons or in bags or luggage, using directed or propagated energy such as ultrasound or microwave, that is reflected or scattered by the materials and objects of interest and that has a wavelength or wavelengths such that the width and/or shape of the reflected beam can be measured at the desired detection distance or range of distances and has a measurable dependence on the size and/or shape of the object.

The preferred method of detection utilizes diffraction, specifically Fraunhofer diffraction.

Fraunhofer diffraction occurs when coherent energy is reflected from a target or passes through an aperture, producing a diffraction pattern. The shape and size of the center lobe of the diffraction pattern are related to the size and shape of the target. In this invention, three measurements across this center lobe may provide enough information to measure the width of the target in the corresponding direction.

If done in two or more directions across the reflection, this technique measures the size of the reflective surface and its rough shape. Once the surface area and shape are known, it is a straightforward matter to obtain the reflectivity of the surface material.

This invention may use energy wave emitters and sensors which are well known to those familiar with the relevant art. Also, techniques for determining reflectivity of an object based upon sensor readings are well known to those familiar with the relevant art.

Because this invention requires only a few sensors (3 sensors is sufficient), the sensors can have large apertures. In practice, this means that in this invention, a single echo pulse is sufficient to obtain good signal to noise ratios and characterize targets at substantial distances.

The operating range for the technique is bounded below by the Fraunhofer condition (Fresnel number less than 1), and above, by the accuracy with which the shape of the reflection is to be measured. The following table lists operating ranges for a 20 cm target and a 20 cm array. The upper bound increases with the size of the array. Both numbers increase with the size of the target. (Terahertz radiation is listed for comparison only.)

| Probe | Range |
|---|---|
| Microwave (10 mm) | 1 m-36 m |
| Ultrasound (7 mm) | 1.4 m-50 m |
| Far Infrared (1 mm) | 10 m-360 m |
| THZ (50 um) | 200 m-7.2 km |

Ultrasound reflectivity is closely related to the hardness of the reflecting surface. Specifically, it depends on the density and elastic modulus of the target material and that of the media (air) in which the incoming and outgoing waves propagate. Consequently hard materials generally have high reflectivity in air. The reflection coefficient for typical metals is ~0.98 and for hard glass is ~0.95 while skin and clothing materials are ~0.5 to ~0.6. This makes ultrasound an ideal probe for an important characteristic of a potentially harmful explosive device.

Figure 7:
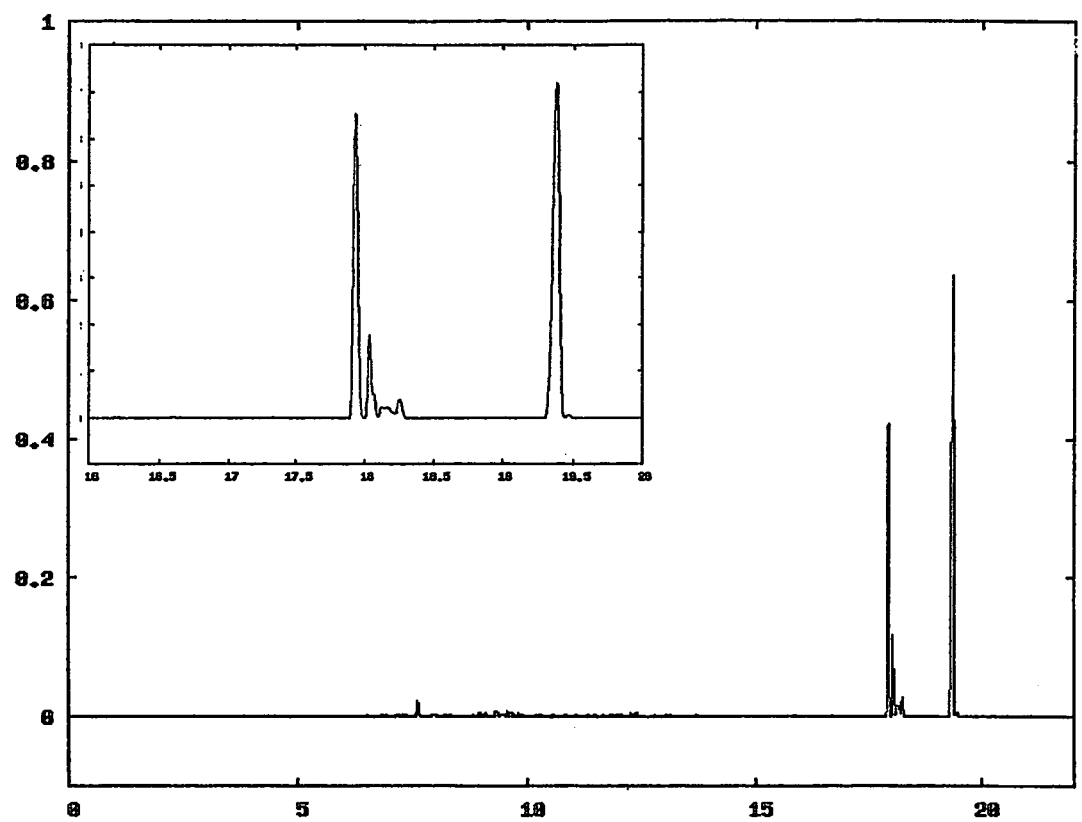
FIG. 7 is a graph of test readings for a person wearing a row of pipes and aluminum foil.
Figure 8:
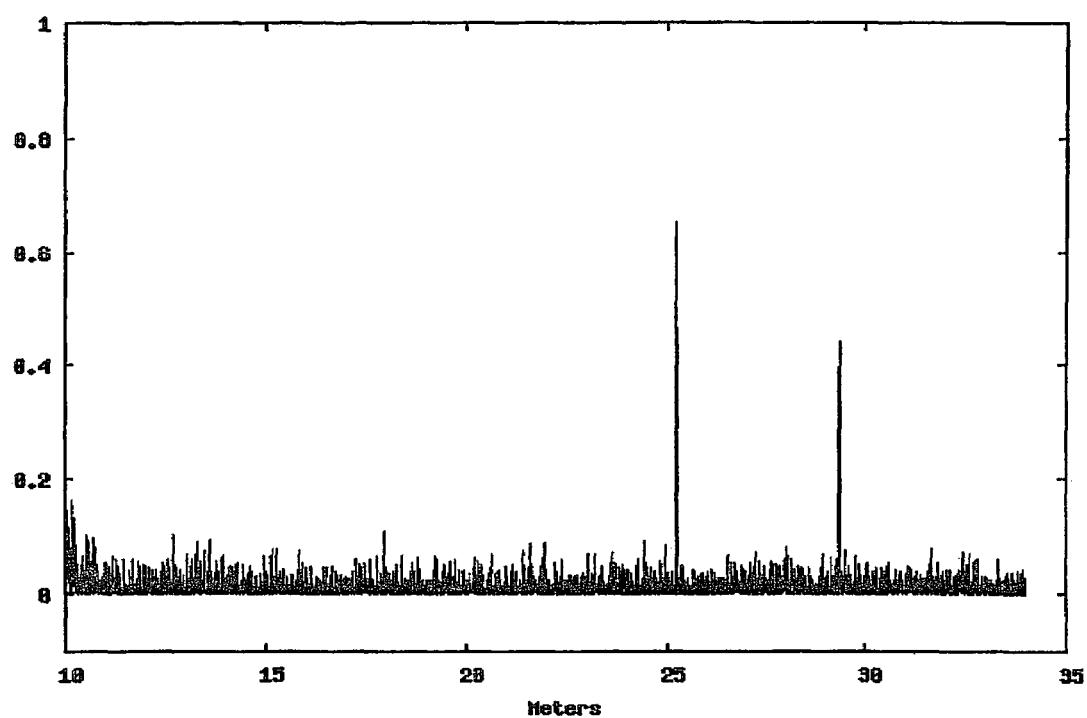
FIG. 8 is a graph of test readings for a person wearing a model exploding vest.

Ultrasound can be projected over distances of tens of meters and produce echoes with useful signal levels. Illustrating data from one channel of an ultrasound phased array, FIG. 7 shows a person wearing an exploding vest model at 18 meters (plus reference target at 19.4 meters); FIG. 8 shows a person wearing another exploding vest model at 25.5 meters (reference target at 29 meters). Target location, size and shape are obtained from the phased array using the technique described above.

In Fraunhofer diffraction, the width and detailed shape of the intensity pattern of reflected or diffracted energy in space, depends on the wavelength of the energy and the size and shape of the reflecting or diffracting surface or aperture. Fraunhofer diffraction is obtained when the distance is large compared to the square of size of the object divided by the wavelength.

$$R > a^2/\lambda$$

Intensity verses angle for Fraunhofer diffraction is depicted in FIG. 1. The zeros and half power width of the sin(x)/x curve (rectangular aperture) are slightly inwards from those of the j1(x)/x curve (elliptical aperture).

The size parameters "a" and "b" may be obtained in approximation from the zeros, the half power width, or from the quadratic coefficient after fitting the central region of the spatial pattern to a polynomial. Similarly, once the fitting parameters are obtained, they may be used to estimate the peak intensity and the integrated total intensity. For this purpose, it is sufficient to measure the echo intensity at just a few points across the echo along each of two orthogonal directions transverse to the direction of propagation of the echo.

The detected object is characterized as follows: the type of material that the surface of the object is made of is roughly identified or characterized by its reflectivity. The reflectivity is approximated by the total reflected energy divided by the energy propagated to the reflecting surface, and normalized by its surface area. The surface area and total reflected energy are obtained as described above. The energy propagated to the object is known by calibration and/or by calculation based on the known parameters of the device that generates and/or transmits the energy to the object (ultrasound or microwave transducer). This typically requires that the location of the object relative to the device has been determined or is known.

The locations of objects, for example people and explosive devices and weapons, that are reflective to the directed or propagated energy, can be obtained using phase and/or timing methods and/or by using a narrowly focused beam. The device can thereby provide spatial information to associate the detected material or object with a specific person from among a group of people and to use in reflectivity measurements as described above.

More detailed information about the shape of the reflecting surface can be obtained by fitting the echo pattern against idealized scattering functions or against a higher order polynomial. With enough sampling locations (a sensor array with a larger number of sensors), the detailed shape of the surface can be obtained by a reverse Fourier transform. As is well known, the scattering pattern for Fraunhofer diffraction is a Fourier transform of the aperture or surface.

The likelihood that a detected object is an explosive device or other weapon is based on crisp or fuzzy logic or pattern recognition techniques applied to the reflectivity, shape, and/or size information. Explosive devices that pose a serious threat are necessarily of some minimum size and encased in materials of some minimum hardness.

Differing parts of the energy spectrum have their own strengths and weaknesses for use in characterizing a detected object. Ultrasound reflectivity is strongly related to hardness, or more specifically elastic modulus and density. Microwave is an appropriate technology for longer distances but is more effective for metals than for non-metallic ceramics and glass. Infrared has the advantage of allowing for more specific material characterization by adding a grating or other dispersive element to the optical path. However, infrared and other short wavelength energies produces Fraunhofer diffraction only at large distances for objects of relevant size, and only from smooth surfaces.

The width of the echo intensity pattern at minimum distances for Fraunhofer diffraction from a 25 cm wide scatter is on order of 25 cm. The sensor array used to measure the echo energy therefore are preferably smaller than 25 cm.

Ultrasound and microwave wavelengths can be used to detect and characterize objects of about 25 cm width by Fraunhofer diffraction from distances on order of 2 meters upwards to the detection limit of the transducers and amplifiers.

Milliwave radiation or Far Infrared at a wavelength of 1 millimeter scattered by a 25 cm wide surface, produces Fraunhofer diffraction at distances greater than 16 meters. In comparison, imaging of concealed objects at distances of tens of meters with milliwave or infrared is difficult, and even at shorter distances, milliwave or Far Infrared imaging is known to require long exposure times. Fraunhofer diffraction is therefore a better way to locate and detect threats at safe stand-off distances.

At infrared wavelengths, for example at 1 um, Fraunhofer diffraction is obtained at distances greater than 16000 meters. CCD's such as used in digital cameras are sensitive to about 900 nm (~0.0000001 m).

For energies and target sizes such that the Fraunhofer limit applies only after some tens of meters, this method can be combined with an enhanced imaging technique. For example, the source that is used to generate reflections can be gated with an imaging detector to collect images with the source on and with it off. The pairs of images can then be subtracted to obtain an enhanced image. Several such images can be added for further enhancement. This enhancement technique described may be combined with the Fraunhofer-based technique to detect weapons and explosive devices across a wider range of distances and with greater accuracy and reliability.

In use, this invention provides sufficient information regarding a detected object's size (area), shape (aspect ratio), and material to determine whether the object may likely be an explosive device. Among the main benefits of this invention are longer detection distances, faster response times, and simple criteria for assessing the likelihood of a threat.

EXAMPLE EMBODIMENTS

1. Ultrasound Device:

An example embodiment using ultrasound is a device with (i) an array of ultrasound air transducers arranged in a configuration such as any of those shown in FIG. 1, (ii) pulse generating electronics, (ii) signal acquisition electronics, (iii) a computer and graphical display, and (iv) a power supply.

Figure 3A:
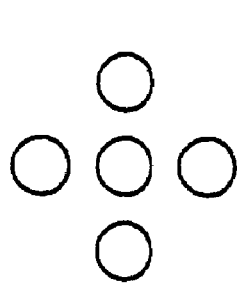
FIGS. 3a-3c are example sensor arrays for measuring reflected energy in two directions transverse to the reflected beam.
Figure 3B:
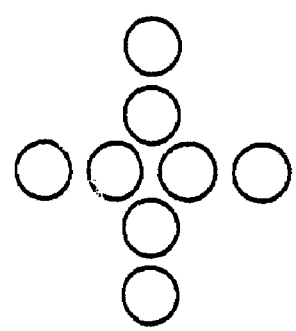
Figure 3C:
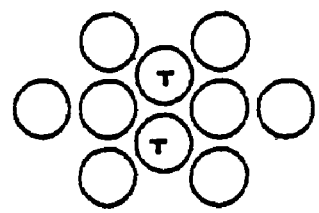
Figure 4A:
FIG. 4a is a diagram of an object and the Fraunhofer-derived representation of its intensity distribution.
Figure 4A:
Figure 4A:
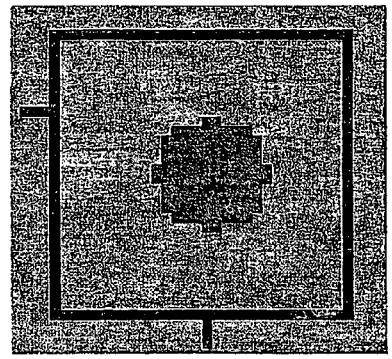
Figure 4B:
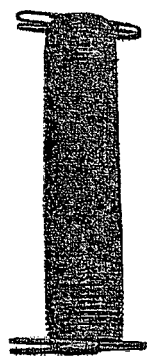
FIG. 4b is a diagram of an object and the Fraunhofer-derived representation of its width.
Figure 4B:
Figure 4B:
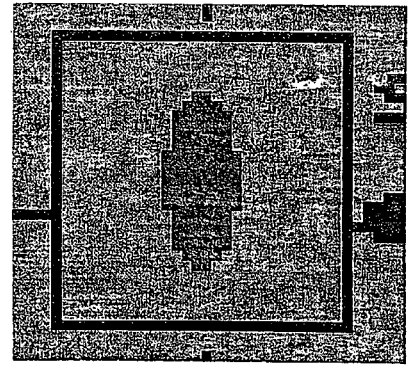
Figures 4C, 4D:
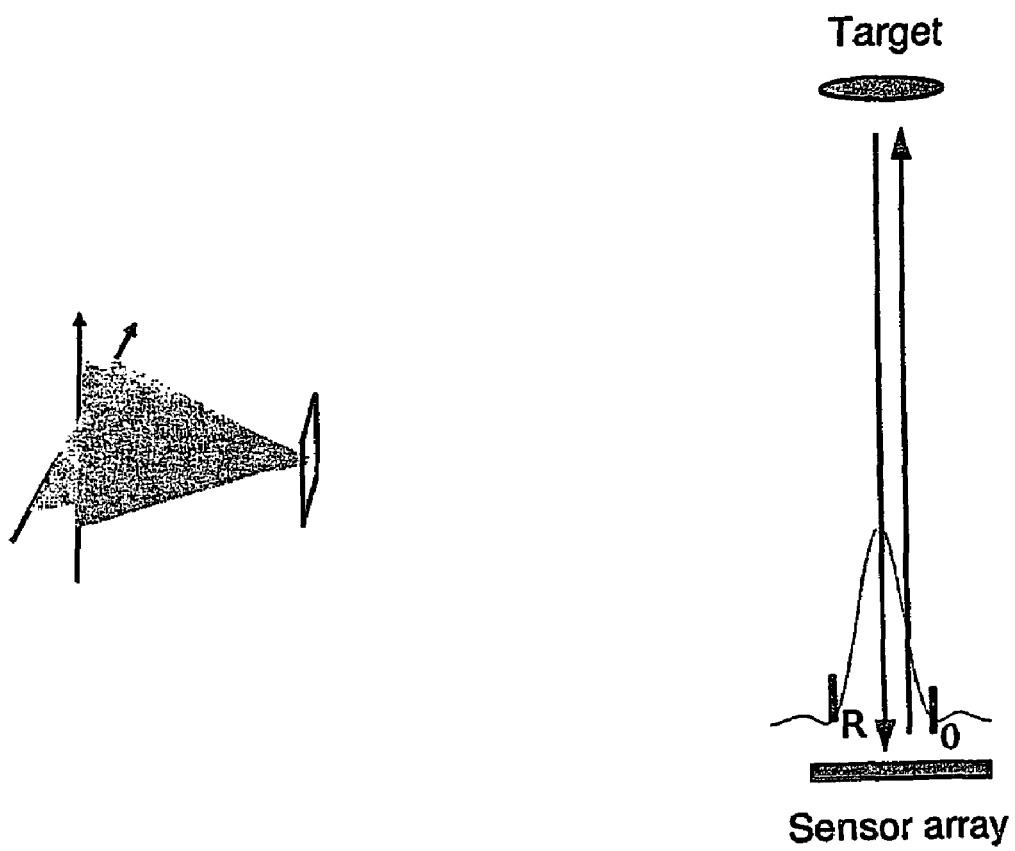
FIG. 4c is a schematic diagram of size being measured in 2 dimensions to determine an object's area and aspect ration (shape).
FIG. 4d is a schematic diagram of an object's reflectivity being obtained.
Figure 5:
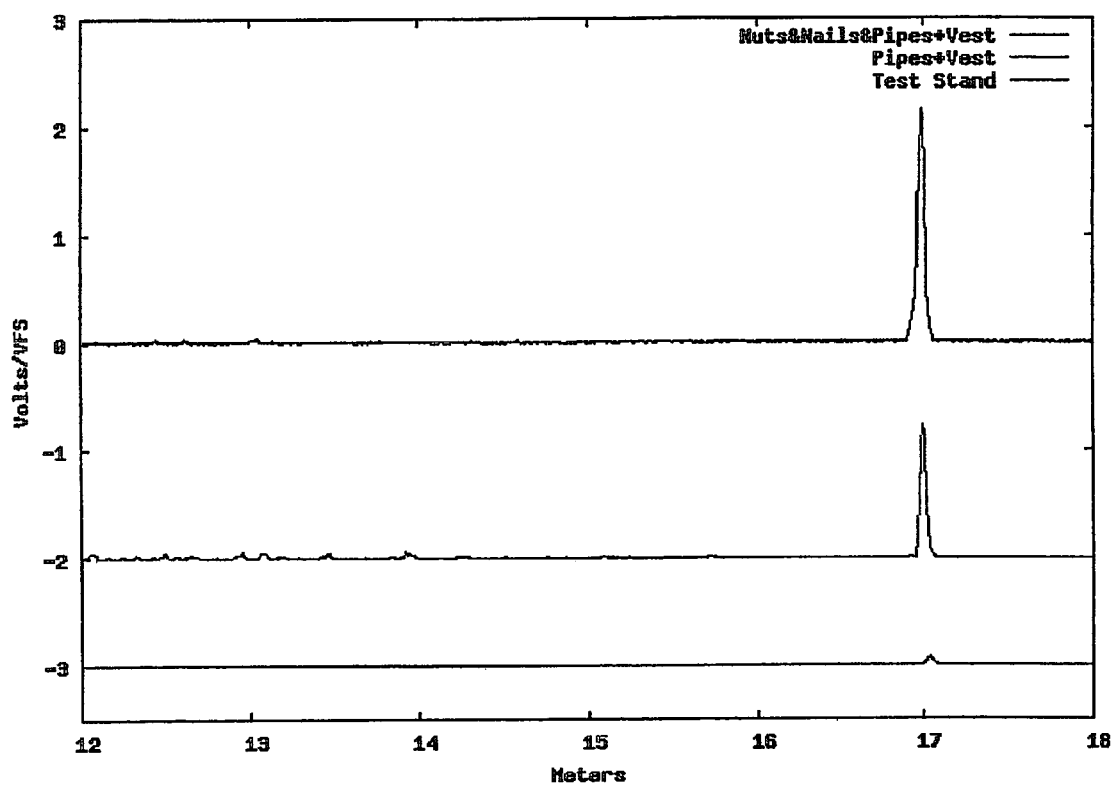
FIG. 5 is a graph of test readings for shrapnel-like objects.
Figure 6:
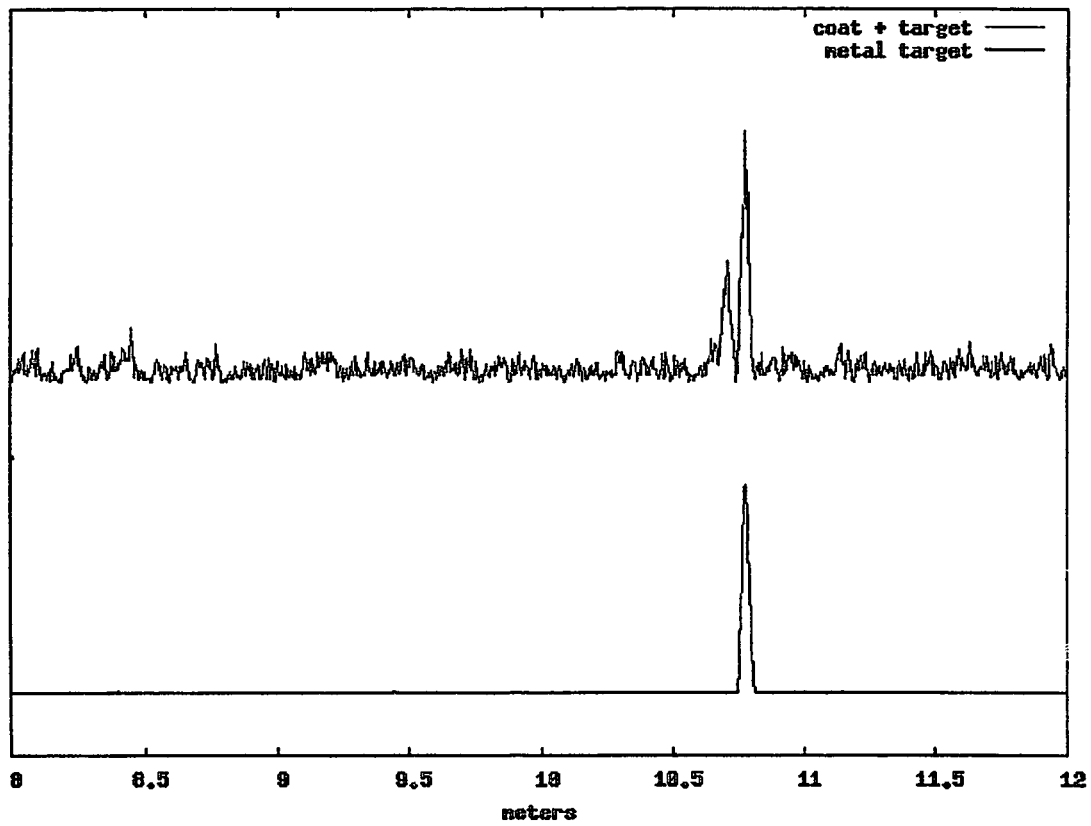
FIG. 6 is a graph of test readings for an hard object concealed under an overcoat.

In FIG. 3, sensor arrays 3a and 3b show transducers that function as dedicated receivers (with transmitters in a separate array) or as dual use transmitters and receivers. In dual use, all transducers function as receivers and one or all also function as transmitter(s). Sensor array 3c shows a single horizontal receiver array with two vertical receiver arrays, and a pair of dedicated transmitters located near the center. Any of these configurations for transducers with a 5 cm diameter, satisfies the maximum width criteria stated above.

The outgoing ultrasound energy can be generated by driving one or more transducers as transmitters. Transmitters operated in pairs or greater numbers, can produce narrow or focused beams depending on the spacing and wavelength. A single transmitter produces a broader beam with spread nominally determined by the wavelength and the effective aperture of the transmitter. A small low power laser can be mounted to the device to facilitate aiming and target identification. A camera can be incorporated and the shutter activated automatically when a threat is detected.

Alarms or threat-likelihood indicators, along with distance and angular offset from beam center, are extracted from the data and displayed in real-time. The center and width of the reflected beam on the sensor array is obtained to determine the total reflected energy and to measure the size and aspect ratio of the reflecting surface. Threat likelihood is assessed from any combination of reflectivity, size and shape using crisp thresholds, fuzzy logic, neural networks or other pattern recognition software that is trained or adapted to recognize likely explosive devices and weapons.

2. Microwave Device:

A microwave embodiment is similar to the above, with transmitting and receiving transducers replaced by microwave transmitters and receivers. Microwave wavelengths are similar to ultrasound and so concepts and methods for measuring the size and reflectivity of the reflecting object and/or surface are applicable and similar for both, as are the size and distribution of sensors.

3. Milliwave Devices:

The geometry and data processing methods for milliwave EMF radiation in the Fraunhofer condition is similar to that described with appropriate sources and receivers and with lengths and sizes meeting the criteria described above.

4. Infrared Devices:

The irradiating energy may be produced by an infrared laser. An infrared sensitive imaging sensor can serve as the detector. In the far field condition, the sensor data is treated as a Fraunhofer diffraction pattern. At shorter distances, the sensor data is processed as an image. Signal enhancement can be obtained by gating the imaging sensor to collect data with the laser on and then off. Subtracting the frames provides an enhanced data set. Adding the enhanced frames provides further enhancement. Applied to an infrared sensor, this method provides enhanced IR imaging.

Spectroscopy may be added to provide chemical or material identification by placing a grating or other dispersive optical element in the optical path.

Other embodiments include without limitation the following:

(1) Detection probability is increased with the number of detection units deployed in a surveillance operation. Multiple units are spaced apart from each other and coordinate by GPS and radio network (e.g., WIFI) for timing and coordinates.

(2) Detection probability is increased with the number of modalities, by combining the strengths of the different modalities: Ultrasound—detects hard materials through clothing; Microwave—detects metals through various materials; and Far Infrared—detects various materials, but is blocked by some materials and background may degrade signal-to-noise ratio.

(3) Detection probability is increased with frame rate. The frame rate is set by the speed of propagation—with ultrasound, ~6 Hz at 30 m; with microwave and infrared, ~10 MHz at 30 m. It is not limited by pulse length, which is generally negligible at less than 0.2% duty cycle. Also, it is not limited by software or current microprocessors, due to ~1 MFLOP per frame theoretical minimum.

Therefore, although this invention has been described with a certain degree of particularity, it is to be understood that the present disclosure is made by way of illustration, and that numerous changes in the details of construction and arrangements of parts may be resorted to without departing from the spirit and scope of the invention.

I claim:

1. Apparatus for detecting a potential explosive device, the apparatus comprising:

sensor means at a distance from the device, the sensor means being capable of sensing an energy wave which is reflected off the potential explosive device, the energy wave having a wavelength, the sensor means comprising a plurality of sensors, the sensor means producing a plurality of energy wave measurements in one-to-one correspondence with the plurality of sensors;

a combination of the potential explosive device, the wavelength, and the distance being characterized by a Fresnel number <1;

analysis means to analyze the energy wave measurements by either fitting the energy wave measurements to a model device, or performing a reverse Fourier transform on the energy wave measurements, thereby producing analysis results; and determination means to determine size, shape, and/or reflectivity of the potential explosive device from the analysis results.

2. A method for detecting a potential explosive device, the method comprising the steps of:

sensing at a distance from the device an energy wave which is reflected off the potential explosive device, the energy wave having a wavelength, the sensing accomplished by a plurality of sensors, thereby producing a plurality of energy wave measurements in one-to-one correspondence with the plurality of sensors;

a combination of the potential explosive device, the wavelength, and the distance being characterized by a Fresnel number <1;

analyzing the energy wave measurements by either fitting the energy wave measurements to a model device, or performing a reverse Fourier transform on the energy wave measurements, thereby producing analysis results; and determining size, shape, and/or reflectivity of the potential explosive device from the analysis results.

* * * * *